(12) United States Patent
Gray

(10) Patent No.: US 7,985,058 B2
(45) Date of Patent: Jul. 26, 2011

(54) METHOD AND APPARATUS FOR MAKING UNIFORMLY SIZED PARTICLES

(76) Inventor: Mark Gray, Long Beach, CA (US)

( * ) Notice: Subject to any disclaimer, the term of this patent is extended or adjusted under 35 U.S.C. 154(b) by 859 days.

(21) Appl. No.: 11/653,618

(22) Filed: Jan. 12, 2007

(65) Prior Publication Data

US 2008/0171077 A1 Jul. 17, 2008

(51) Int. Cl.
*B01F 5/20* (2006.01)
(52) U.S. Cl. ......... 425/7; 425/6; 425/8; 425/10; 425/86; 425/145; 264/5; 264/9; 264/13; 264/14; 424/489
(58) Field of Classification Search ................. 425/5, 6, 425/7, 10, 86, 145, 169, 453, 456, 457, 458, 425/804; 264/4.1, 4.3, 4.32, 4.33, 4.6, 4.7, 264/14, 233, 408, 412, DIG. 37, 5, 7, 9, 11, 264/12, 13; 424/450, 451, 489, 641; 366/176.1
See application file for complete search history.

(56) References Cited

U.S. PATENT DOCUMENTS

| | | | | |
|---|---|---|---|---|
| 2,428,911 | A | * | 10/1947 | Gunnell ............................ 264/4 |
| 2,436,439 | A | * | 2/1948 | Lincoln et al. ..................... 425/5 |
| 3,885,940 | A | * | 5/1975 | Levecque et al. ................ 65/467 |
| 3,962,383 | A | * | 6/1976 | Hagiwara et al. .................. 264/4 |
| 4,268,293 | A | * | 5/1981 | Levecque et al. ................ 65/464 |
| 4,323,455 | A | * | 4/1982 | Tanaka et al. ............ 210/321.75 |
| 4,481,157 | A | * | 11/1984 | Morishita et al. ............... 264/4.1 |
| 4,661,458 | A | * | 4/1987 | Berry et al. ..................... 435/401 |
| 4,692,284 | A | * | 9/1987 | Braden ........................... 264/4.3 |
| 4,764,317 | A | * | 8/1988 | Anderson et al. ................. 264/4 |
| 4,814,274 | A | * | 3/1989 | Shioya et al. .................. 435/174 |
| 4,902,450 | A | * | 2/1990 | Morrison ............................ 264/4 |
| 5,000,887 | A | | 3/1991 | Tenzel et al. |
| 5,040,960 | A | * | 8/1991 | Shioya et al. ...................... 425/5 |

(Continued)

FOREIGN PATENT DOCUMENTS

WO WO2008/089112 A3 7/2008

OTHER PUBLICATIONS

Avestin Applications, website printout from http://avestin.com/efapplications.html; May 30, 2006, 3 pages.

(Continued)

*Primary Examiner* — Joseph S Del Sole
*Assistant Examiner* — Seyed Masoud Malekzadeh
(74) *Attorney, Agent, or Firm* — Christie, Parker & Hale, LLP

(57) ABSTRACT

A method and apparatus for making substantially uniformly sized liposomes and other small particles are provided. Droplets of a first liquid are ejected into a laminar flow of a second liquid, each droplet having a volume of from 0.97V to 1.03V, where V is the mean droplet volume and 1 fL≦V≦50 nL, wherein the first and second liquids are no more than sparingly soluble in one another, and wherein the first liquid contains a solute dissolved, dispersed, or suspended therein; and the first liquid is then removed to form a plurality of substantially uniformly sized particles. In one embodiment, the apparatus includes liquid inlet and outlet channels, a plurality of transverse liquid channels extending from the liquid inlet to the liquid outlet channel, a plurality of nozzles in liquid flow communication with the plurality of transverse liquid channels, one or more nozzle actuators coupled to the plurality of nozzles, and an evaporator coupled to the liquid outlet channel.

19 Claims, 9 Drawing Sheets

U.S. PATENT DOCUMENTS

| | | | |
|---|---|---|---|
| 5,260,002 A * | 11/1993 | Wang | 264/4.1 |
| 5,540,936 A * | 7/1996 | Coe et al. | 424/450 |
| 5,653,996 A * | 8/1997 | Hsu | 424/450 |
| 5,741,478 A * | 4/1998 | Osborne et al. | 424/9.52 |
| 6,103,271 A * | 8/2000 | Morrison et al. | 424/490 |
| 6,217,849 B1 | 4/2001 | Tournier et al. | |
| 6,258,858 B1 * | 7/2001 | Nakajima et al. | 516/73 |
| 6,281,254 B1 * | 8/2001 | Nakajima et al. | 516/53 |
| 6,331,314 B1 * | 12/2001 | Klinksiek et al. | 424/450 |
| 6,534,018 B1 * | 3/2003 | Baker et al. | 422/128 |
| 6,572,893 B2 * | 6/2003 | Gordon et al. | 424/489 |
| 6,576,023 B2 * | 6/2003 | Nakajima et al. | 264/14 |
| 6,623,671 B2 * | 9/2003 | Coe et al. | 264/4.3 |
| 6,689,464 B1 * | 2/2004 | Lanze et al. | 428/402 |
| 6,855,277 B2 * | 2/2005 | Baker et al. | 264/4.3 |
| 6,855,296 B1 * | 2/2005 | Baker et al. | 422/130 |
| 6,998,074 B1 | 2/2006 | Radulescu | |
| 7,083,572 B2 | 8/2006 | Unger et al. | |
| 7,268,167 B2 * | 9/2007 | Higuchi et al. | 516/9 |
| 7,432,110 B2 * | 10/2008 | Kikuchi et al. | 436/177 |
| 2001/0006689 A1 * | 7/2001 | Ishikawa et al. | 425/269 |
| 2002/0050660 A1 * | 5/2002 | Coe et al. | 264/4.1 |
| 2003/0094715 A1 * | 5/2003 | Suzuki et al. | 264/4.1 |
| 2003/0124033 A1 * | 7/2003 | Baker et al. | 422/128 |
| 2003/0215514 A1 * | 11/2003 | Platz et al. | 424/489 |
| 2004/0081689 A1 * | 4/2004 | Dunfield et al. | 424/451 |
| 2005/0163723 A1 * | 7/2005 | Foster et al. | 424/46 |
| 2006/0240093 A1 | 10/2006 | MacLachlan et al. | |
| 2007/0034568 A1 * | 2/2007 | Foster et al. | 210/634 |
| 2007/0228588 A1 * | 10/2007 | Noritomi et al. | 264/4.1 |
| 2008/0061463 A1 * | 3/2008 | Guillot et al. | 264/53 |
| 2008/0171078 A1 | 7/2008 | Gray | |
| 2010/0025872 A1 * | 2/2010 | Hashiba | 264/4.1 |

OTHER PUBLICATIONS

Avanti Polar Lipids, Inc.; product listing from website: http://www.avantilipids.com/extruder.html; Mar. 5, 2004; 3 pages.

Rand; *Structural Parameters of Aqueous Phospholipid Mixture*; website printout from http://aqueous.labs.brocku.ca/lipid/; Membrane Biophysics Laboratory, St. Catharine's, Ontario, Canada; Feb. 14, 2004; 11 pages.

Souza et al.; *Liposome Stability Verification by Atomic Force Microscopy*; Rev. Adv. Mater.Sci.5 (2003) 34-40, 7 pages.

*Lipid Bilayers and Cell Membranes*; excerpt from University of Chicago website http://www.uic.edu/classes/phys/phys461/phys450/MARKO/N016.html; Jun. 29, 2005, 7 pages.

*Liposomes and Vesicles, AFM Imaging as a Tool to Visualize Liposomes and Vesicles*; PSIA, Inc. website article, www.psiainc.com; Jun. 2005; 11 pages.

Keller, et al.; *Thermodynamic Aspects and Biological Profile of CDAN/DOPE and DC-Chol/DOPE Lipoplexes*; Research Article; American Chemical Society; Dec. 2002 and Jan. 2003; 11 pages.

Tagawa, et al.; *Characterszation of LMD Virus-like Nanoparticles Self-assembled From Cationic Liposomes, Adenovirus Core Peptide μ (mu) Plasmid DNA*; Research Article; Gene Therapy, vol. 9 (2002); 564-576; 13 pages.

Alhaique, et al.; *Solvent[1] H NMRD Study of Biotinylated Paramagnetic Liposomes Containing Gd-bis-SDA-DTPA or Gd-DMPE-DTPA*; Research Article; F. Inorganica Chimica Acta 331 (2002) 151-157; 7 pages.

Fellowes, et al.; *Amelioration of Established Collagen Induced Arthritis by Systemic IL-10 Gene Delivery*; Research Article; Gene Therapy, vol. 7 (2000); 967-977; 11 pages.

Thurston, et al.; *Cationic Liposomes Target Angiogenic Endothelial Cells in Tumors and Chronic Inflammation in Mice*; Research Article; The American Society for Clinical Investigation, Inc., vol. 101, No. 7, Apr. 1998; 1401-1413; 13 pages.

Hainfeld; *Gold Liposomes*; Research Paper/ web-page article: www.nanoprobes.com/MSA96LIP.html; Department of Biology, Brookhaven National Laboratory, Upton, NY; May 23, 2003; 3 pages.

Goins et al.; *The Use of Scintigraphic Imaging as a Tool in the Development of Liposome Formulations*; Research Article; Progress in Lipid Research Jan.-Mar. 2001;40(1-2):95-123; 29 pages.

Alhaique, et al.; *Solvent[1] H NMRD Study of Biotinylated Paramagnetic Liposomes Containing Gd-bis-SDA-DTPA or Gd-DMPE-DTPA*; Research Article; F. Inorganica Chimica Acta 331 (2002) 151-157; 7 pages.

Singh, et al.; *Fluorescent Liposome Flow Markers for Microscale Particle-Image Velocimetry*; Research Article; Anal. Chem., (2001), 73, 1057-1061; 5 pages.

Düffels, et al.; *Cationic Lipids for Gene Therapy, Part III[=], Synthesis of High-Mannose Type Neoglycolipids: Active Targeting of Liposomes to Macrophages in Gene Therapy*; Research Article; Chem. Eur. J. 2000, vol. 6, No. 8; 1416-1430; 15 pages.

Themis, et al.; *Enhanced In Vitro and In Vivo Gene Delivery Using Cationic Agent Complexed Retrovirus Vectors*; Research Article; Gene Therapy vol. 5 (1988); 1180-1186; 7 pages.

Nakhla, et al.; *Issues Associated with Large-Scale Production of Liposomal Formulations*; web article, Drug Delivery Technologies; www.drugdeliverytech.com; Mar. 5, 2004; 10 pages.

Miller; *Gene Therapy*; Research Article; webpage excerpt from www.thebiotechclub.org/industry/emerging/gene_therapy.php; GSAS Harvard Biotechnology Club Mar. 3, 2004; 6 pages.

*Alza's Stealth® Liposomal Technology: Current Therapies and Future Opportunities*; webpage article: www.alza.com; Delivery Times, Issues and Opportunities, vol. 2, No. 1; Alza Corporation; 12 pages.

Bramwell, et al.; *Liposome/DNA Complexes Coated with Biodegradable PLA Improve Immune Responses to Plasmid Encoding Hepatitis B Surface Antigen*; Research Article; Immunology vol. 106 (2002) 412-418; 7 pages.

Frézard; *Liposomes: From Biophysics to the Design of Peptide Vaccines*; Braz J Med Biol Res, Feb. 1999, vol. 32(2) 181-189; 9 pages.

Kucerka, et al., Determination of bilayer thickness and lipid surface area in unilamellar dimyristoylphosphatidylcholine vesicles from small-angle neutron scattering curves: a comparison of evaluation methods, Eur Biophs J (2004) 33: pp. 328-334.

International Preliminary Report on Patentability and Written Opinion for International Application No. PCT/US08/050945, filed on Jan. 12, 2008, 6 pages.

International Preliminary Report on Patentability and Written Opinion for International Application No. PCT/US08/050946, filed on Jan. 12, 2008, 4 pages.

* cited by examiner

METHOD AND APPARATUS FOR MAKING UNIFORMLY SIZED PARTICLES

CROSS-REFERENCE TO RELATED APPLICATION

This application is related to the U.S. patent application entitled, "Uniformly Sized Liposomes," filed on an even date herewith, the contents of which are incorporated by reference herein.

FIELD OF THE INVENTION

Nanoscale and microscale technologies have experienced enormous growth and commercial interest within the last decade. Recent technical developments suggest that uniform small particles have the potential to change product design, functionality and manufacture. The nano- and micro-particles currently available in a limited assortment of size ranges and chemistries have already found a variety of commercial applications, and the ability to better control particle size, as well as to expand upon the particle chemistries available, are expected to provide numerous societal benefits in the long run. The present invention provides a new approach to manufacturing uniform small particles, and should greatly facilitate the development of new or improved products in the energy, chemical, medical, consumer products, and other industries where a greater degree of control over particle size dispersity and shape is needed.

BACKGROUND OF THE INVENTION

While a great number of therapeutic compounds are discovered every year, the clinical applications of these compounds are often limited by their failure to reach the site of action. A further problem is the toxicity of many drugs at non-target sites. Often, compounds with desirable therapeutic effects have been identified and characterized only to be sidelined by their toxicity profiles. Selective drug targeting would not only reduce systemic toxicity but would also improve drug action by concentrating the therapeutic compound in selected cell or tissue targets. The delivery of drugs to specific target sites is therefore of great interest in clinical science.

Unfortunately, drug delivery technologies have not kept pace with target identification and novel compound synthesis. Delivery problems are especially lacking in the rapidly evolving area of RNA and DNA-based therapeutic intervention.

Increasingly, liposomes are being used to deliver drugs and other agents to target sites in cells. Liposomes are hollow, spherical vesicles comprised of membranes that behave as two-dimensional fluids. In a spherical model, steric stability is heightened at a particular particle diameter for any particular lipid formulation based on the free energies associated with slight deformations of the membrane. Adsorption, spreading, fusion, self-healing, and other mechanical properties of liposomes are recognized as important performance indicators toward their application as delivery vehicles.

In general, liposomes can be formed with outer diameters ranging from 20 to 1000 nm (1 µm), more typically 40-500 nm, with ~100 nm diameter liposomes being particularly desirable for many biological applications. Liposomes smaller than about 20 nm are physically untenable, while liposomes larger than about 1 µm in diameter tend to be unstable and aggregate over time. Liposome size has a direct effect on payload encapsulation efficiency in the case of an active loading scheme whereby preformed liposomes absorb active ingredients from the surrounding media into their interiors, with smaller sized vesicles being more efficient than larger ones. To a large extent, liposome size determines the sites of action of liposome-cell interaction. Size affects not only how and where the liposomes enter a cell, but also whether they reach a particular cell at all. For some therapeutic applications, efficient tissue targeting requires that the liposomes be able to circulate in the bloodstream for a long period of time until a proper target is encountered.

In vivo, liposomes that are too large as a direct result of the manufacturing process, or that agglomerate into larger units as a result of secondary instabilities in solution, will tend to become entrapped in areas simply based on size. For example, the liver removes larger particles from the bloodstream (larger than 200 nm diameter) because of vasculature sized to act as a physical filter. For this reason, many liposome formulations have been created with liver tissue targeting in mind simply because large particles end up in the liver, and this observation leads to the illusion of a natural affinity of liposomes for liver cells. In fact, oversized liposomes merely become entrapped in the liver because of their size. In any application not targeting the liver, liver localization would have the detrimental effect of removing active material from the intended site of deposition, as well as increasing the likelihood of off-targeting and side effects by misplacing an otherwise therapeutic payload.

In some therapeutic applications, liposomes are administered by intravenous injection, and liposome size—and charge—directly influence the clearance of liposomes from the patient's bloodstream. Generally, the longest half-lives are obtained when liposomes are small in diameter (<0.05 µm). It has also been found that "liquid" vesicles are more rapidly removed from blood circulation than "rigid" ones. The behavior of liposome preparations given by alternative parental routes, such as intraperitoneal, subcutaneous or intramuscular route is also influenced by the distribution of liposome size.

In many therapeutic applications, and particularly in systemic delivery and tissue and cell targeting, liposome size is a critical parameter of therapeutic effectiveness. In order for liposomes to function efficiently as vectors for a given biological application, they need to be as monodisperse as possible, i.e., have as narrow a size distribution as possible. In general liposomes are measured in terms of their (outer) diameters, with little discussion in the literature of internal volume. The literature suggests that a collection of liposomes is considered uniformly sized if the liposomes' outer diameters are polydisperse by only ±10%, i.e., 90-110 nm outer diameters for a collection of liposomes having a mean diameter of 100 nm. The fact that this is considered "good" is shocking, as a difference of 10% in diameter corresponds to roughly a 92% difference in internal volume (if, e.g., one assumes an 8 nm thick lipid layer).

Obtaining the ideal liposome size is therefore a matter of determining the proper chemistry for a given biological application and sizing the particles at exactly those dimensions—a tall order for existing technologies.

Clearly, liposome size distribution is a critical parameter with respect to the pharmacological and pharmacodynamic behavior of biologically active substances that are site-specific targeted in vivo. Although various methods of making small unilamellar vesicles (SUVs) are available, from a process perspective, the formation of stable SUVs with a narrow and predictable size distribution remains a challenge. Commercial liposome sizing systems typically operate by making a number of passes through various size reduction methodologies, that utilize shear force and/or ultrasonic energy dispersion to reduce the size of the liposomes to an approximated average. The most common means of resizing is by passing the liposomes a number of times through a membrane. The production of liposomes with very true homodispersity (i.e., substantially monodisperse), has not been reported, and there is no protocol available in the literature for the production of such particles, let alone a protocol for achieving narrow size distributions under the demanding conditions and in the large volumes required for pharmaceutical production.

An unexpected benefit of the regular sizing of liposomes is the ability to control charge density. Charge density is determined by both the internal payload and external lipid envelope. The lipids comprising the envelope are chosen according to their charge, and the ratio of the constituent lipids is determined according to the charge desired. Determining and quantizing the desired overall charge of the loaded particle is particularly important for delivery of highly charged payload such as DNA. Since DNA payloads are often large, and a single copy of the DNA is loaded per liposome, the negative charge is best neutralized by an envelope of a specific size in order to achieve a desired charge balance. Slight variations in charged liposome size distribution could therefore profoundly affect biodistribution. Considering this fact, and not anticipating that liposomes could be made to have a very uniform size/charge, one author wrote that this factor will serve to "preclude or at least limit the in vivo use of many potentially effective lipid-based DNA delivery vectors."

The limitations of current technology have a detrimental impact on clinical research and commercial utilization of liposome treatments. When polydisperse liposome formulations are used, valuable markers, isotopes, drugs, and other reagents and payloads are wasted, as they do not reach their intended target and are effectively lost. This retards the development of new therapies (in terms of wasted opportunities and increased time in the lab), and increases the cost of commercial applications (more liposomes are required, as much of the liposomes are the wrong size to be effective).

Accordingly, there is a very strong need in the pharmaceutical, biotechnology, and cosmetics industries for substantially homogenous liposome formulations, particularly unilamellar liposomes that exhibit diameters in the 100 to 200 nm range, and an efficient, robust system for reproducibly generating uniformly sized liposomes and other small particles. In addition, with current liposome and particle manufacturing techniques, it is exceedingly difficult, if not impossible, to know exactly—or even approximately—how many particles are in a given container of any size. This is because available manufacturing processes are batch processes, and only after the batch is created can a person find out what the yield was, and this is accomplished by running a sample through a particle size analyzer (PSA), or by doing some electron microscopy. Both of these methods are expensive, error-prone, and generally unreliable. A digital manufacturing process would be a significant improvement over the art, as it would enable liposomes and other small particles to be produced with great accuracy and precision.

SUMMARY OF THE INVENTION

The present invention provides a method and apparatus for making a collection of small particles having a narrow size distribution, such as a collection of substantially uniformly sized liposomes. According to a first aspect of the invention, the method comprises (a) forming droplets of a first liquid in a laminar flow of a second liquid, each droplet having a volume of from 0.97V to 1.03V, where V is the mean droplet volume and $1\ fL \leq V \leq 50\ nL$, and wherein the first and second liquids are, at most, sparingly soluble (more preferably, substantially immiscible) in one another, and the first liquid contains a solute dissolved, dispersed, or suspended therein; and (b) removing the first liquid to form a plurality of substantially uniformly sized particles. For liposomes, the method comprises forming droplets of a first liquid containing one or more lipids dissolved, suspended, or dispersed therein by ejecting the first liquid into an aqueous laminar flow, wherein the first liquid is no more than sparingly soluble (preferably, substantially immiscible) in water, and wherein each droplet has a volume of from 0.97V to 1.03V, where V is the mean droplet volume and $1\ fL \leq V \leq 50\ nL$; and allowing the lipids to self-assemble into substantially uniformly sized liposomes by removing the first liquid. In one embodiment, the substantially uniformly sized liposomes have a mean outer diameter of from 20 nm to 1 μm.

In a second aspect of the invention, an apparatus for making substantially uniformly sized particles comprises a liquid inlet channel; a liquid outlet channel; a plurality of transverse liquid channels extending from the liquid inlet channel to the liquid outlet channel; a plurality of nozzles in liquid flow communication with the plurality of transverse liquid channels; and one or more nozzle actuators coupled to the plurality of nozzles. Optionally, an evaporator, such as a membrane pervaporation unit, is coupled to the liquid outlet channel, directly or indirectly. For example, in one embodiment, a pervaporation unit is coupled to the liquid outlet channel via a separate collection reservoir or conduit.

The method and apparatus are particularly well-suited for making a substantially monodisperse collection of liposomes having a mean outer diameter, D, of from 20 nm to 1000 nm, with at least 95% of the liposomes having an outer diameter of from 0.97 D to 1.03 D, for example, a collection of liposomes having a normal distribution of diameters, with a mean outer diameter, D, of from 25 nm to 1000 nm, and a standard deviation $\leq 0.015$ D.

In one embodiment of the invention, substantially uniformly sized droplets are generated using nozzles, actuators, software, and electronics associated with "drop on demand" inkjet printers. By controlling the electric impulses to the actuator(s), very precisely sized volumes of fluid are generated and then ejected as droplets into a laminar flow of a substantially immiscible, or at least no more than sparingly soluble, liquid, and then carefully evaporating away or otherwise removing the first liquid. For example, liposomes are made by ejecting well-defined droplets of solvent—containing lipids dissolved, dispersed or suspended therein—through the nozzles of the apparatus into a laminar flow of water or other aqueous medium in the transverse liquid channels; collecting the resulting droplets; and then carefully removing the solvent to facilitate self-assembly of the lipids into liposomes. Advantageously, the liposomes' narrow size distribution is correlated to the initial concentration of lipids-in-solvent and the size of the droplets ejected from the nozzles.

BRIEF DESCRIPTION OF THE DRAWINGS

Various aspects, embodiments, and advantages of the invention will become better understood when reference is made to the accompanying drawings, wherein.

DETAILED DESCRIPTION

Figure 1:
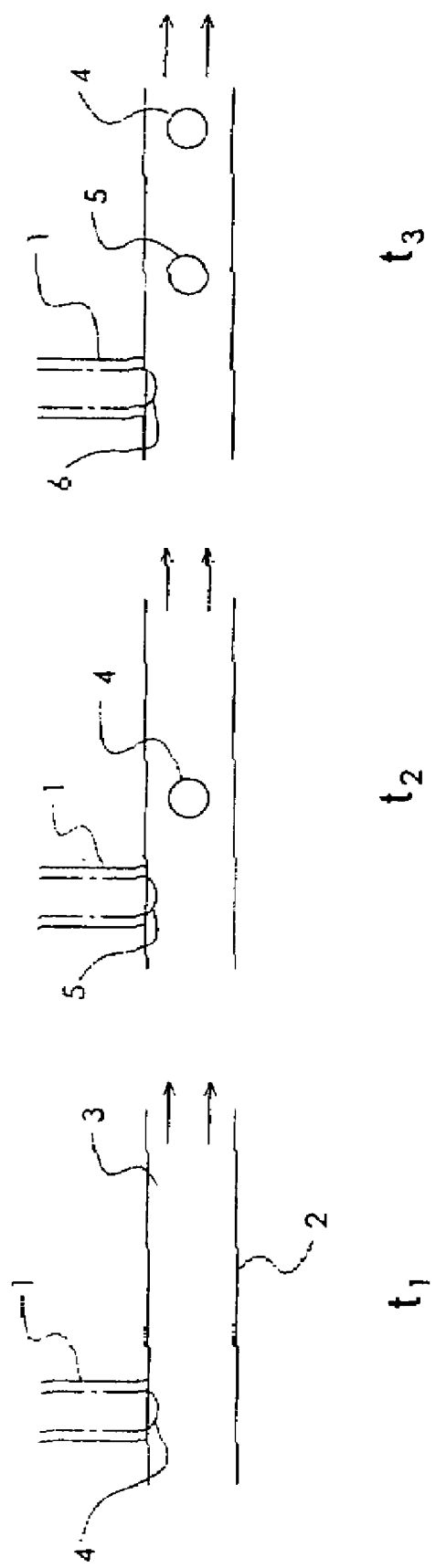
FIG. 1 is a schematic diagram of a nozzle ejecting a droplet of liquid into a laminar flow of a second liquid, according to one embodiment of the invention.

According to one aspect of the invention, a method of making substantially uniformly sized particles comprises: (a) forming droplets of a first liquid in a laminar flow of a second liquid, each droplet having a volume of from 0.97V to 1.03V (preferably 0.98V to 1.02V, more preferably 0.99V to 1.01V) where V is the mean droplet volume, 1 fL$\leq$V$\leq$50 nL, and wherein the first and second liquids are, at most, sparingly soluble in one another, and the first liquid contains a solute dissolved, dispersed or suspended therein; and (b) removing the first liquid to form a plurality of substantially uniformly sized particles. As used herein, the term "sparingly soluble" refers to a solubility of 10% or less, under the conditions of temperature and pressure encountered during droplet formation. In some embodiments, the first and second liquids are substantially immiscible in one another.

In the case where the uniformly sized particles are liposomes, the method comprises forming droplets of a first liquid containing one or more lipids dissolved, suspended, or dispersed therein by ejecting the first liquid into a laminar flow of a second liquid, i.e., water or other aqueous medium, wherein the first liquid is no more than sparingly soluble in the second liquid, and wherein each droplet has a volume of from 0.97V to 1.03V (preferably 0.98V to 1.02V, more preferably 0.99V to 1.01V), where V is the mean droplet volume and 1 fL$\leq$V$\leq$50 nL; and allowing the lipids to self-assemble into substantially uniformly sized liposomes by removing the first liquid. (A payload, carried in the first and/or the second liquids, or added after the liposomes form, may also be present.) In one embodiment, the liposomes thus formed have a mean outer diameter, D, of from 20 nm to 1000 nm, and at least 95% of the liposomes have an outer diameter of from 0.97 D to 1.03 D, more preferably from 0.98 D to 1.02 D, most preferably from 0.99 D to 1.01 D. In some embodiments, even tighter size distributions are provided, e.g., at least 96%, at least 97%, at least 98%, or at least 99% of the liposomes have an outer diameter of from 0.97 D to 1.03 D, more preferably from 0.98 D to 1.02 D, most preferably from 0.99 D to 1.01 D.

The mean outer diameter of the collection of liposomes is brought as close as desired to a particular value (e.g., 100 nm, 200 nm, etc.), which can be selected so that the liposomes are correctly sized to deliver a payload to a desired cellular site of action. For example, in one embodiment, D=100 nm. More generally, the collection of liposomes has a mean outer diameter, D, of from 20 nm to 1000 nm, from 25 to 500 nm, from 50 to 200 nm, from 75 to 125 nm, from 90 to 110 nm, or (e.g.) from 95 to 105 nm, with a narrow size distribution (optionally Gaussian) about the mean diameter, D; i.e., at least 95%, at least 96%, at least 97%, at least 98%, or at least 99% of the liposomes have outer diameters whose values deviate from D by no more than 3%, 2%, or, most preferably, 1%.

The outer diameters of individual liposomes, as well as the mean outer diameter of a collection of liposomes, can be determined using a suitable measurement technique, for example, photon correlation spectroscopy, freeze fracture and electron microscopy, or by using the "Coulter principle," whereby voltage potential fluctuation in a small orifice determines particle size. Alternatively, other techniques for determining particle size and size distributions, presently known or discovered in the future, are used. In general, photon correlation spectroscopy is preferred over electron microscopy because it is significantly faster.

Advantageously, however, actual measurement is not required, as the method of manufacture is designed to ensure that the liposomes have the desired mean diameter and narrow size distribution, as described below.

It is contemplated that all manner of liposomes can be prepared with a desirably narrow size distribution as described herein, regardless of the lipid(s) and/or other chemical species that comprise the liposomes. The liposomes can be monolayer vesicles, or bilayer vesicles (formed, e.g., of amphipathic, aka amphiphilic, lipids), and can be multilamellar or, more preferably, unilamellar. Phospholipids, such as phosphatidylethanol amines, are a type of amphipathic lipid capable of self-assembling into liposomes in water. A non-limiting list of lipids capable of self-assembling into liposomes is found in U.S. Pat. No. 7,083,572, col. 20, lines 23-59, which is hereby incorporated by reference herein.

The collection of liposomes can be prepared with or without a payload, including payloads that function as biological labels, probes, or markers. Unless otherwise noted, "payload" refers to a substance that be carried by, in, or with liposomes. "Patient" refers to a human or non-human, mammalian or non-mammalian animal, in-patient, out-patient, or self-administering individual. "Pharmaceutical" refers to a therapeutic, prophylactic, diagnostic, or similar agent or agents, including substances that function as labels, markers, probes, and the like. A payload can be "administered" orally, by injection, by inhalation, transdermally, or by any other medically acceptable means for delivering a pharmaceutical to a patient. "Sufficient in quantity to be administered as a pharmaceutical" means that the collection of liposomes is large enough to be manipulated and delivered as such to a patient.

Non-limiting examples of payloads include amino acids, proteins, enzymes, natural and synthetic nucleic acids (e.g., DNA, RNA, siRNA, plasmids, etc.), dyes, contrast agents, radiolabeled compounds, fluorescent compounds, medicaments, organic compounds, inorganic compounds (e.g., gold and/or other metallic particles; semiconducting particles, e.g., nanodots), and mixtures of these and/or other substances. The payload can have any desired chemical form, including atomic, molecular, and ionic. In one embodiment, the collection of liposomes is carried in a liquid medium, which typically is water or some other aqueous medium. For example, the aqueous medium can further comprise a pH buffer. Non-limiting examples of buffers include saline, ammonium sulfate, HEPES (4-(2-hydroxyethyl)-1-piperazineethanesulfonic acid), TRIS (tris(hydroxymethyl)aminomethane), and mixtures thereof.

The liquid medium itself can also carry or include a payload, which can be the same as or different from the payload carried by the liposomes, if any.

Where a payload is included, it can be carried by or coupled to the liposomes in a number of ways familiar to persons skilled in the art. For example, the payload can be carried within the hollow interior of the liposomes (which, in most cases, also hold water). The payload can be coupled to or carried on the inner and/or outer walls of the liposomes. The payload can be enmeshed within the mono- or bi-layers that form the liposomes. In some embodiments, the payload extends from the interior to the exterior of the liposomes.

As indicated above, in view of the tight size distribution, the collection of liposomes can be characterized by a mean outer diameter and a standard deviation there from. Thus, in one embodiment of the invention, a composition for delivering a payload to a patient comprises a collection of liposomes sufficient in quantity to be administered as a pharmaceutical (for example, $10^7$ or more liposomes), wherein the liposomes have a mean outer diameter, D, of from 25 nm to 1000 nm, with a standard deviation less than or equal to 0.015 D. In some cases, the collection of liposomes will have a spread of outer diameters that can be characterized by a so-called normal distribution, with a probability function, P(x), where x is distance (outer diameter) in nanometers. Systemic errors in the liposomes production process (and/or the manufacturing process(es) used to make various components of the apparatus used to make the collection of liposomes), as well as other factors, may, in some cases, result in the liposomes having a size distribution other than that characterized by the classic Gaussian probability function.

For liposome production, generally the first liquid is hydrophobic and the second liquid is aqueous. Thus, in one embodiment, the first liquid comprises an organic solvent. Nonlimiting examples include hydrocarbons (e.g., hexane), halogenated hydrocarbons (e.g., dichloromethane, chloroform, trichloroethylene, freon, etc), aromatic compounds (e.g., toluene), ethers (if sufficiently hydrophobic), mixtures thereof, as well as other organic solvents or compounds or mixtures of such materials). Mixtures of organic compounds can be used. Of particular interest is an embodiment in which the first liquid comprises one or more organic compounds, i.e., an organic solvent in which a desired lipid or lipids can be dissolved, dispersed, or suspended, and the second liquid is water or an aqueous medium. The second liquid may also include a pH buffer. Nonlimiting examples include saline, ammonium sulfate, HEPES (4-(2-hydroxyethyl)-1-piperazineethanesulfonic acid), TRIS (tris(hydroxymethyl)aminomethane), and mixtures thereof.

For applications in which non-liposomal particles are formed, the first and second liquids are selected from a broad array of compounds and mixtures thereof. Nonlimiting examples include hydrocarbons, halogenated hydrocarbons, alcohols (e.g., methanol, ethanol, isopropyl alcohol, etc.), ketones (e.g., acetone), amines, polymers, other organic compounds, inorganic compounds, and other substances. For example, in one embodiment, the first liquid comprises mercury, and the second liquid comprises a liquid that it is substantially immiscible with (or no more than sparingly soluble in) mercury. In another embodiment, the first liquid comprises at least one oil.

The hydrophobicity/hydrophilicity of the first and second liquids also can be reversed from that just described. Thus, in another embodiment of the invention, the first liquid is aqueous and the second liquid is hydrophobic. For example, the second liquid can comprise at least one organic solvent.

In some embodiments (e.g., in the formation of liposomes), the first liquid contains a solute dissolved, dispersed or suspended therein. Non-limiting examples of solutes include polymers, lipids (especially amphipathic lipids), organic compounds, inorganic compounds, and mixtures thereof. Of particular interest are solutes comprising one or more amphipathic lipids capable of forming bilayer liposomes. One or more additional agents (e.g., detergents, surfactants, antioxidants, etc.) can also be present.

As characterized, the invention contemplates that droplets having a mean volume of from anywhere from 1 fL to 50 nL are formed. In some embodiments, however, the mean droplet volume is confined to a narrower range, namely, from 1 pL to 50 pL. In one embodiment of the invention, droplets of the first liquid are formed by ejecting the first liquid through at least one nozzle directly into a laminar flow of the second liquid. This is schematically illustrated in FIG. 1. A nozzle 1 is in fluid flow communication with a channel 2 through which moves a laminar flow of a second liquid 3. At time $t_1$, the nozzle ejects a first droplet 4 of a first liquid into the channel and is carried downstream by the second liquid. At time $t_2$, a second droplet 5 of the first liquid is ejected through the nozzle into the channel and also is carried downstream. At time $t_3$, a third droplet is ejected from the nozzle into the channel and carried downstream. The first, second, and third droplets of the first liquid are substantially immiscible with (or no more than sparingly soluble in) the second liquid, and each droplet is separated in space by a distance determined by the nozzle ejection rate and the rate of laminar flow of the moving liquid in the channel. The flow of liquids in the channel is substantially laminar (non-turbulent), and a sufficient delay is provided between each droplet such that the droplets substantially retain their integrity as they flow through the channel. Consequently, when they are collected downstream and the first liquid is evaporated away (e.g., in a membrane pervaporation unit), the solute that is contained in the droplets becomes concentrated. In the special case where the solute comprises one or more lipids capable of forming liposomes, removal of the first liquid brings the lipids into contact with the aqueous second liquid, and the lipids spontaneously self-assemble and form liposomes, the diameters of which are neatly correlate to the droplet volume and the initial concentration of lipids in the first liquid.

Substantially uniformly sized small particles are obtained by carefully removing the first liquid (or a substantial quantity thereof) from the droplets, so that what is left are discrete particles formed of or from the solute(s), and having a very tight size distribution. The first liquid can be removed in a number of ways. In one embodiment, the first liquid is removed by simple evaporation: The droplets of first liquid carried in the second liquid are drawn off into an open reservoir and allow to off gas the first liquid. In another embodiment, the first liquid is removed by pervaporation, i.e., membrane pervaporation. Pervaporation is particularly suited for liposome formation, where the ratio of solvent to lipids is extremely high and it is desirable to minimize disruption of the droplets as the solvent is stripped away For example, in the case where the first liquid is an organic (hydrophobic) solvent containing solute(s), and the second liquid is water, a feed of (solvent+solute) droplets, in water, is brought in contact with a thin, hydrophobic membrane, which is permeable to the solvent, but not to water. The feed (upstream) side of the membrane is more or less at ambient pressure, while the downstream side of the membrane is brought under reduced pressure by, e.g., connecting it to a vacuum pump. The permeate (solvent) is pulled through the membrane and, preferably, captured by a cold trap and, optionally, collected and recycled). As more solvent is removed from the water, the droplets continue to lose more solvent, until substantially all that is left is the retentate: in this case, water and solute particles, or water and particles formed from the solute, e.g., liposomes, which can be drawn off and collected.

Pervaporation membranes can be selected based on the identity and properties of the first and second liquids. Non-limiting examples of pervaporation membranes include supported and self-supporting (e.g., rigid) materials, for example, ceramic membranes (including coated ceramic hybrids).

Where it is desirable to include one or more payloads in admixture with, or carried by or in, the liposomes, the payload can be introduced in a number of ways. For example, the payload can be carried by the first and/or the second liquid, or introduced into the system after droplet formation, or even after pervaporation.

Figure 2:
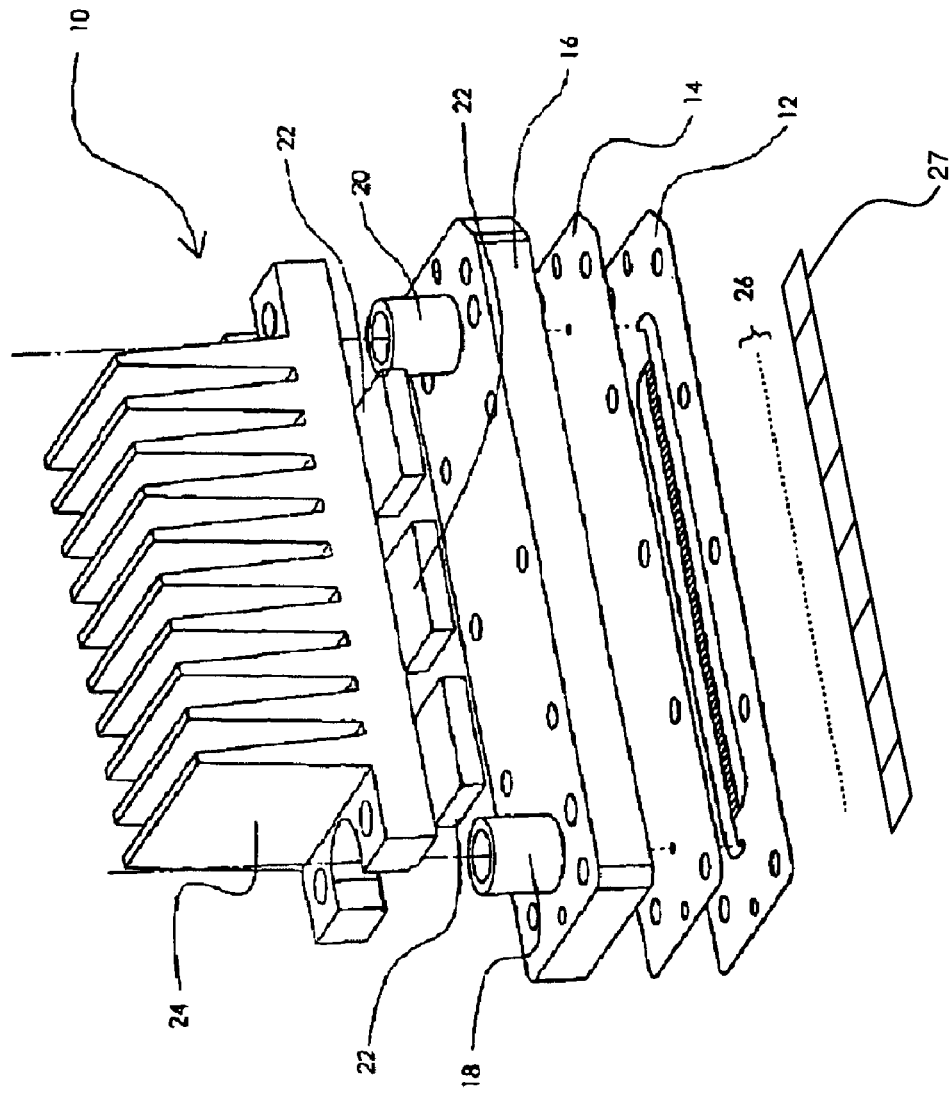
FIG. 2 is a schematic, partially exploded view of one embodiment of an apparatus for making substantially uniformly sized particles in accordance with the invention.

FIGS. 2 through 10 illustrate one embodiment of an apparatus for making substantially uniformly sized liposomes and other small particles according to the invention. Referring to FIG. 2, there is shown an apparatus 10 having a bottom microfluidics channel plate 12, a top microfluidics channel plate 14, an inlet/outlet manifold 16 (having a liquid inlet port 18 at one end and a liquid outlet port 20 at the opposite end), thermoelectric heater/coolers 22, and a radiator 24 (which are thermally coupled to the inlet/outlet manifold and provide a way of supplying and/or removing heat to and/or from the apparatus). A plurality of nozzles 26 are positioned below the bottom microfluidics channel plate and provide a means for ejecting precisely controlled droplets of a first liquid into the apparatus. In the embodiment shown, 64 nozzles are depicted schematically. One or more nozzles can be provided as an inkjet printer head (e.g.) or as stand alone nozzles capable of ejecting discrete droplets. The apparatus also includes one or more nozzle actuators (not shown), which provide a carefully controlled impulse to eject a precisely sized bubble (droplet) of the first liquid through each nozzle. Non-limiting examples of nozzle actuators include piezoelectric actuators and thermal bubble actuators. In one embodiment, each nozzle is driven by a separate actuator. In another embodiment, a single actuator drives two or more nozzles. Inkjet printer heads, nozzles, and actuators, and the associated electronics and software to drive them, are well known in the art.

Figure 3:
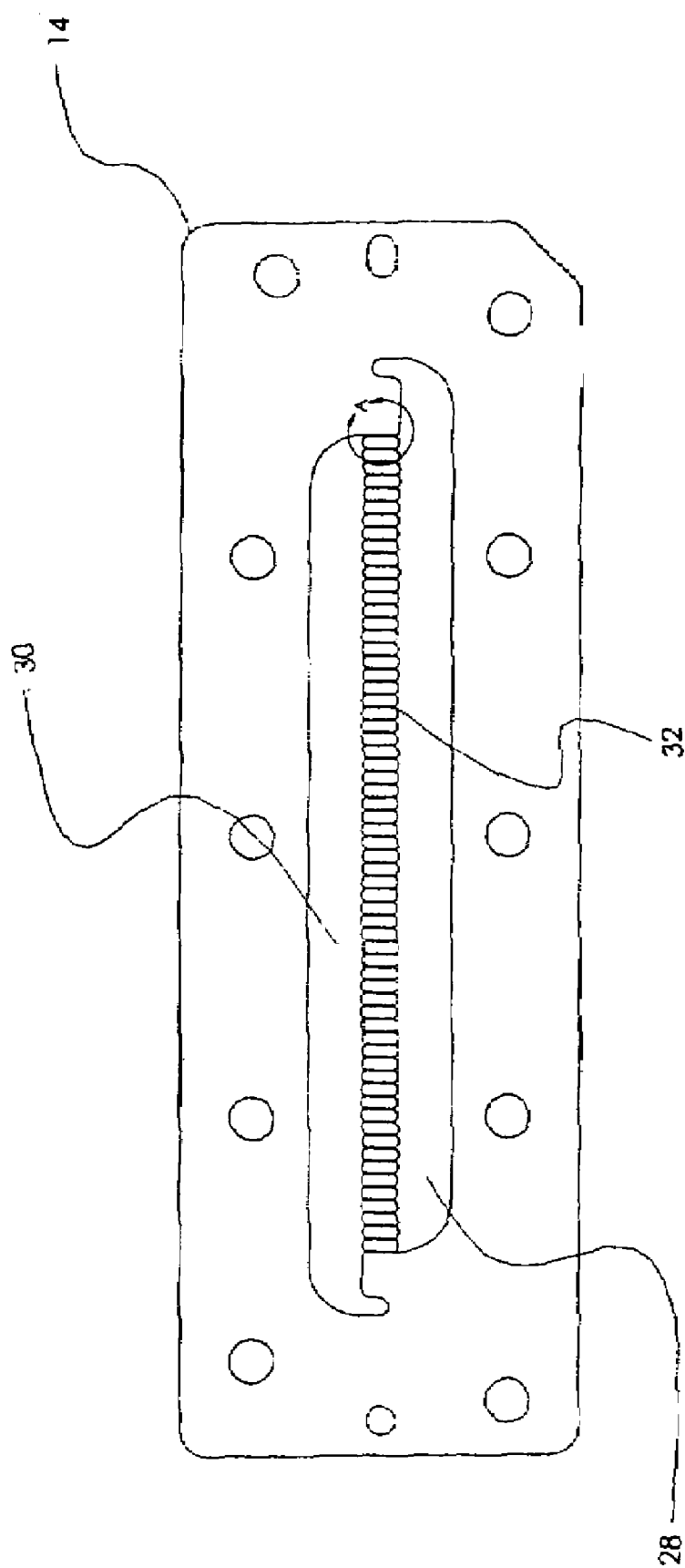
FIG. 3 is a plan view of a microfluidics channel plate, a component of one embodiment of the invention.

The top and bottom microfluidics channel plates 14, 12 mate in fluid-tight fashion and together form a microfluidics channel at the plates' interface. Referring now to FIG. 3, the top microfluidics channel plate 14 is shown in greater detail. The plate includes an inlet channel 28, an outlet channel 30, and a plurality of transverse liquid channels 32 that extend from the inlet channel to the outlet (exit) channel. In the embodiment shown, 64 such transverse channels are provided. One end of the inlet channel includes an opening that allows liquid to flow into the channel from the inlet port 18 in the inlet/outlet manifold. Similarly, one end of the exit channel has an opening that allows liquid to exit to the outlet port 20 in the inlet/outlet manifold. The outlet port, in turn, can be coupled to a pervaporation unit (not shown), either directly or via a fluid conduit.

Figure 5:
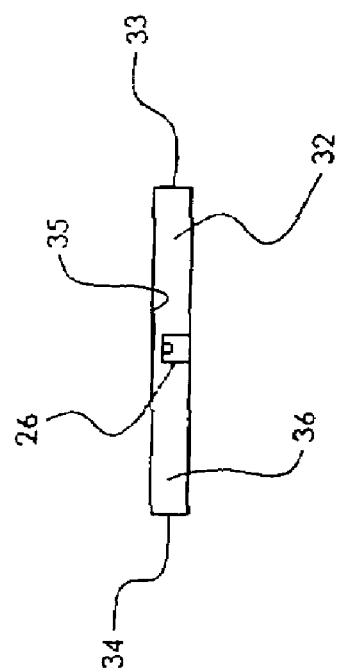
FIG. 5 is a more highly magnified close-up of a portion of the plate shown in FIG. 4 taken along line B-B.
Figure 4:
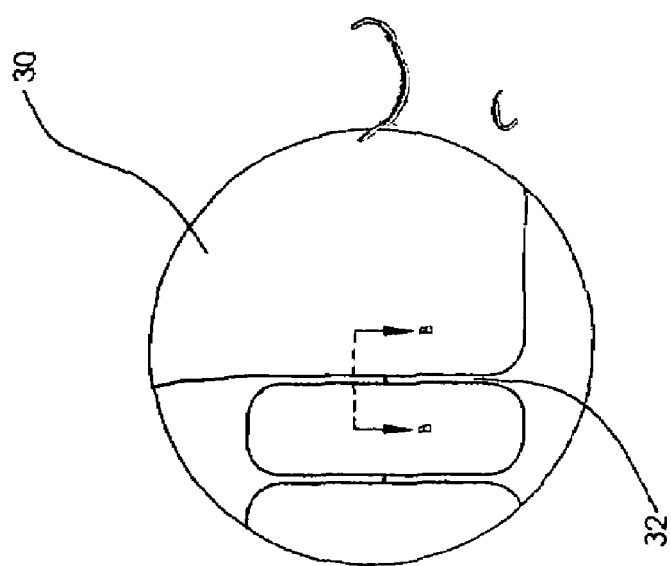
FIG. 4 is a close-up view of a portion of the plate of FIG. 3 denoted by circle A.
Figure 6:
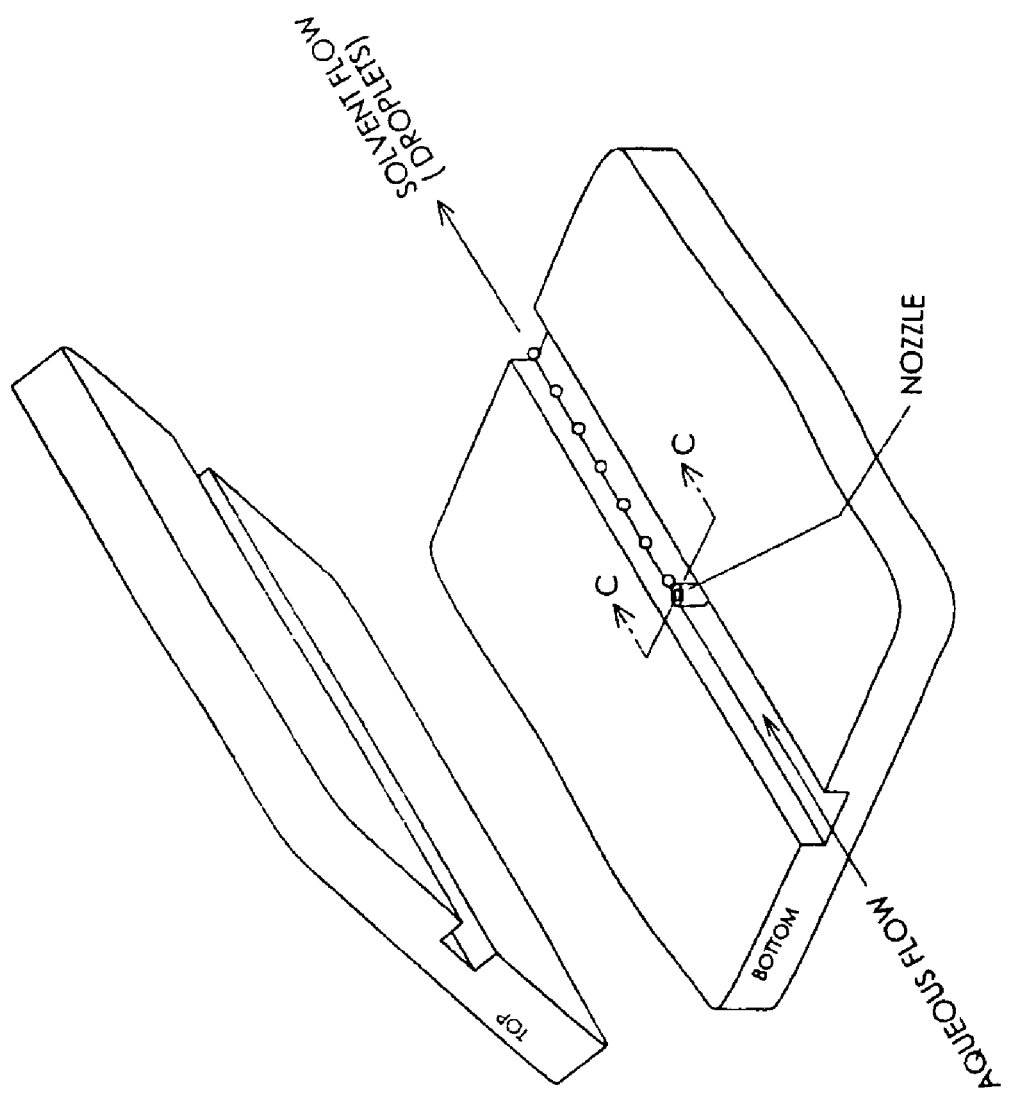
FIG. 6 is an exaggerated schematic view of a nozzle ejecting droplets into a microfluidics channel according to one embodiment of the invention.
Figure 7:
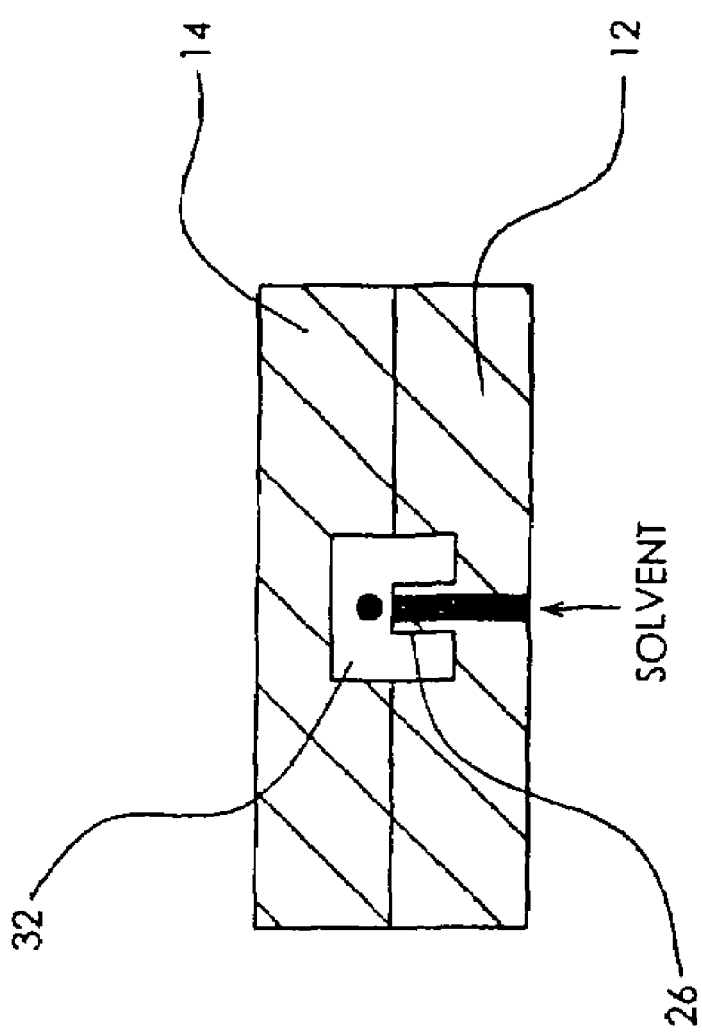
FIG. 7 is a sectional view of a portion of FIG. 6, taken along line C-C.

Additional detail of the transverse liquid channels and their relationship with the plurality of nozzles is shown in FIGS. 4 and 5. As indicated, the transverse liquid channels 32 are substantially smaller in cross-section than the inlet and outlet channels. In FIG. 5, a cross-sectional view taken along lines B-B, one of the nozzles 26 is shown extending into one of the transverse liquid channels 32. The transverse liquid channel has opposite sidewalls 33, 34, a bottom 35 formed by the bottom microfluidics channel plate, and a top 36 formed by the top microfluidics channel plate. The nozzle extends from the bottom of the transverse liquid channel up into the interior of the channel through an opening (not shown) in the bottom of the bottom microfluidics channel plate. FIGS. 6 and 7 are exaggerated schematic views showing a portion of a top microfluidics channel plate 14 rotated out and away from the bottom microfluidics channel plate 12, revealing one of the plurality of transverse liquid channels 32, with a nozzle 26 protruding up from the bottom of the channel into the interior. This is also shown in FIG. 7, an exaggerated sectional view taken along line C-C.

It will be appreciated that the dimensions of the inlet and outlet channels, the transverse liquid channel, and the nozzles are exceedingly small, with even smaller nozzle diameters (i.e., the inner diameter of the ejection orifice at the tip of each nozzle). Nonlimiting examples include: transverse channels: 1-30 μm (with small dimensions being preferred); inlet and outlet channels: the same size as, or slightly larger than, the transverse channels; nozzle orifices: 0.01-30 μm, preferably 0.01-10 μm. Small transverse channels permit small particles to be obtained and require less buffer in the system, yielding a higher titre of the final composition, i.e., more particles (liposomes) per milliliter. Smaller nozzles permit smaller droplets to be generated, which should yield a greater number of particles in the final composition per unit volume, e.g., more liposomes per mL.

In the embodiment shown in FIGS. 2 through 7, each of the plurality of nozzles has substantially the same nozzle diameter, and each nozzle has a proximal end coupled, directly or indirectly, to one or more liquid reservoirs (not shown), and a distal end that extends into the interior of a corresponding one of the plurality of transverse liquid channels. Alternate embodiments, however, are also within the scope of the invention. For example, the nozzles need not necessarily have the same nozzle diameter. In addition, each nozzle can be flush with the bottom of a corresponding transverse liquid channel, or some nozzles can protrude into, while others are flush with, a corresponding transverse liquid channel, etc. Two or more nozzles can extend into a single transverse channel.

In general, the materials used to construct the microfluidics channel plates are selected to be non-corrosive in the presence of water and organic solvents, and cleaning regimens of soap, steam, and/or chlorides. Nonlimiting examples include NiCo (nickel cobalt alloy) and stainless steel. In one embodiment, the top and bottom plates are held together in a press fit to form a fluid-tight assembly by threaded fasteners (not shown) that span the radiator to the I/O manifold, with the thermoelectric heater/coolers held in compression between them. Optionally, a thermally conductive lubricant can be applied to the upper and/or lower surfaces of the heater/coolers to facilitate heat transfer between the radiator and the I/O manifold.

The thermoelectric heater/coolers allow the temperature of the microfluidics channels and the nozzles to be controlled, which can be desirable for a number of reasons. First, controlling the temperature allows the surface tension at the first liquid/second liquid interface (e.g., the solvent/water interface at the nozzle orifices) to be modulated. If the fluids are cold, the surface tension will be greater. Second, in the microfluidics channels, viscosity is controlled via temperature. Third, in the general mixing of the fluids, it is important to maintain a good separation between the different fluid types. The droplets, if too "hot" might tend to "blur" into the other liquid, due to an increase in solubility.

In some embodiments, where heat-sensitive compounds are present, it is contemplated that the apparatus will be operated above or below room temperature (~25° C.), in the range of 30 to 200° F. (−1 to 92° C.), with 30 to 80° F. (−1 to 26° C.) being most desirable for most liposome chemistry. In other embodiments, where more thermally stable materials are employed, e.g., where the particles being formed are solid organic polymer beads, the apparatus may be operated at even higher temperatures, e.g., 300° F. (147° C.). Accordingly, it is contemplated that the apparatus will be operated at a temperature of from 20 to 300° F. (−7 to 147° C., or, alternatively, 20 to 200° F. (−7 to 92° C.), or alternatively, 20 to 100° F. (−7 to 37° C.).

It is also contemplated that the pressures of the first and second liquids in the apparatus is carefully controlled. In one embodiment, each of the liquids has, independently, a pressure of 100 psi or less, e.g., from 10-100 psi; more typically 20-40 psi (excluding the pervaporation unit, which, in one embodiment, is expected to operate at a higher pressure). In another embodiment, either or both liquids have a pressure that exceeds 100 psi. The two liquids can be supplied by a pressure supply system, which is coupled to the nozzles and the inlet port of the inlet/outlet manifold.

Figure 8:
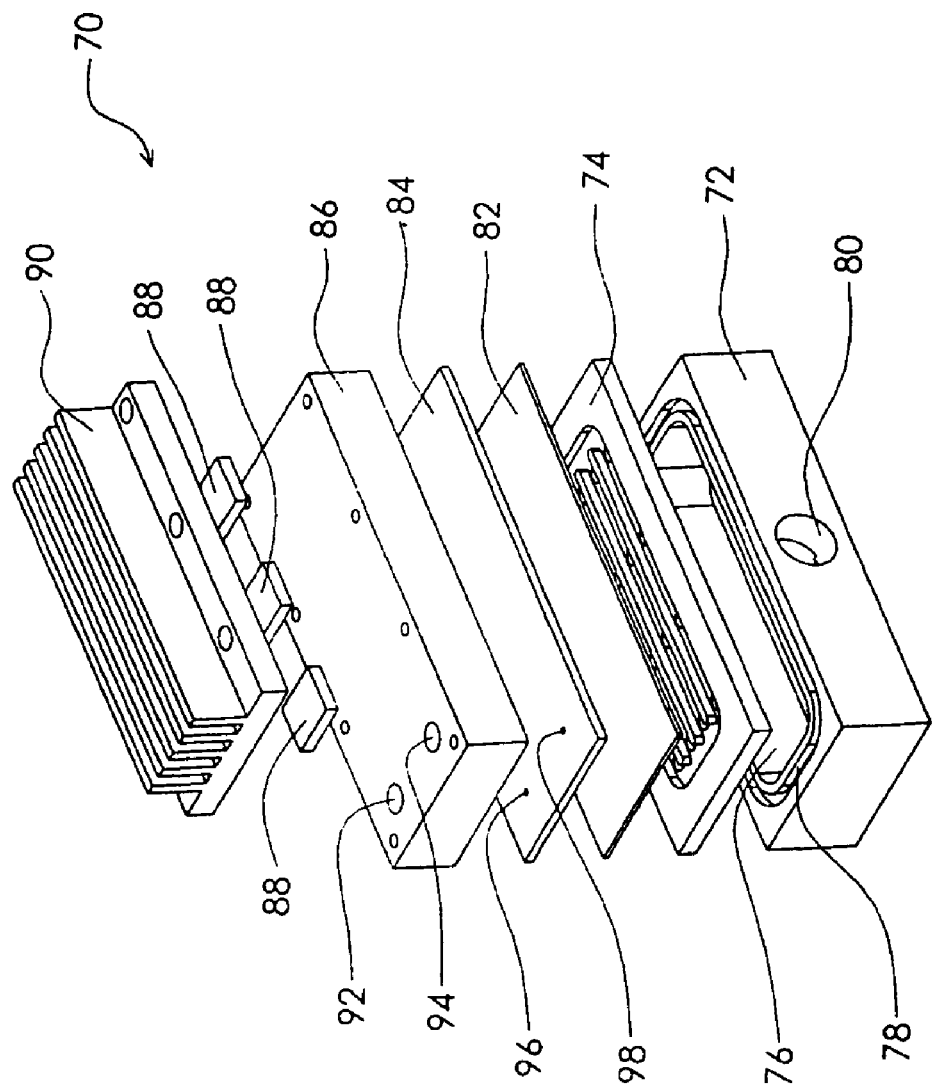
FIG. 8 is a schematic diagram of one embodiment of a pervaporation unit used in the practice of the invention.

One embodiment of a pervaporation unit is depicted in FIG. 8. The pervaporation unit 70 includes a lower housing 72 and a membrane support plate 74, which together define a vacuum chamber 76. An O-ring (not shown) seated in a channel 78 along the top periphery of the lower housing ensures that a gas-tight seal is maintained between the housing and the membrane support plate. A vacuum port 80 in the lower housing can be connected to a vacuum pump (not shown) and permits gasses to be evacuated from the vacuum chamber to create and maintain a reduced pressure inside the vacuum chamber. In some embodiments, a cold trap (not shown) is located in line between the vacuum port and the vacuum pump, allowing the permeate (e.g., organic solvent) to be captured for disposal or, more preferably, reuse. A selectively permeable membrane 82 is sandwiched between a fluid flow plate 84 and the membrane support plate 74. An inlet/outlet manifold 86 sits atop the fluid flow plate. Thermoelectric heaters/coolers 88 and a radiator 90 allow heat to be supplied to or removed from the pervaporation unit as needed. A fluid inlet port 92 in the inlet/outlet manifold can be coupled to the outlet port of the droplet generator (FIG. 2), while pervaporation products (e.g., liposomes in water, emulsions, solid polymer beads, nanodots, other small particle systems) can be removed from the unit through a fluid outlet port 94. Inlet and outlet ports 96 and 98 are also provided in the fluid flow plate 84, and provide access to the selectively permeable membrane 82. Peripheral components such as a power supply and a microprocessor or other logic controller (not shown) can be coupled to the thermoelectric heaters/coolers and, as with the droplet generator, allow the temperature of fluids in the unit to be closely monitored and controlled. In one embodiment, the flow of fluids through the droplet generator and the pervaporation unit, and the temperature of the fluids, are carefully regulated by a shared microprocessor or other logic controller.

Figure 9:
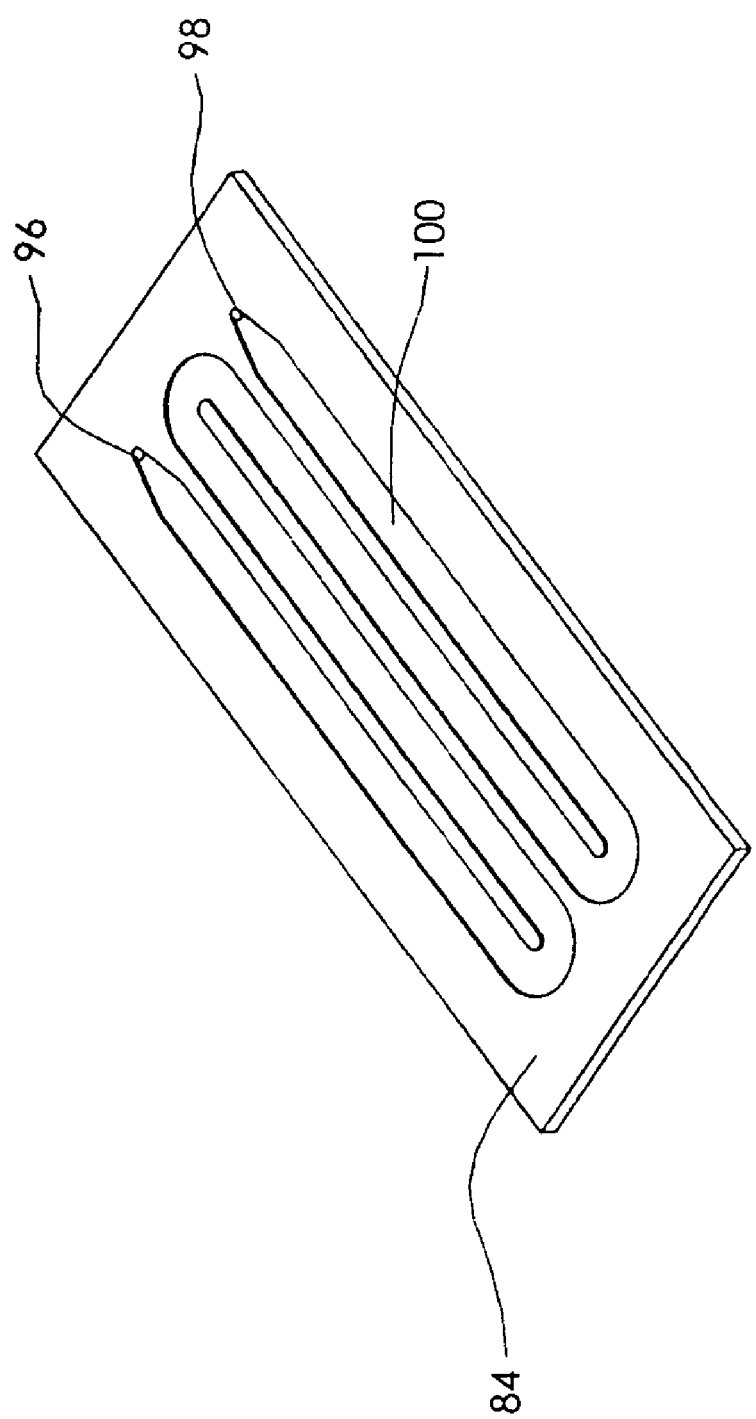
FIG. 9 is a schematic diagram of a fluid flow plate according to one embodiment of the invention.

FIG. 9 illustrates the underside of the fluid flow plate 84, which faces the selectively permeable membrane 82. The plate includes openings 96 and 98 and a serpentine channel 100 cut into the lower face, the channel extending from one opening to the other. The serpentine channel provides an extended pathway for a laminar flow of droplets of the first liquid carried by the second liquid, and serves to minimize turbidity while maintaining maximum surface contact between the moving liquids and the selectively permeable membrane. Reduced pressure on the underside of the membrane (facing the enclosed chamber) facilitates the steady, yet controlled, removal of the first liquid along the length of the serpentine channel.

In operation, the pervaporation unit is brought to and maintained at temperature, which may be higher or lower than ambient and within the range of 20 to 170° F. (−7 to 76° C.), as dictated by the physical chemistry of the combination of fluids being separated. For the production of liposomes, in which the lipids must self-assemble, the preferred temperature range is 32 to 80° F. (0 to 26° C.). For the production of other particle types, the range may be much higher because of the inherent stability of the chemistry and more efficient operation of the pervaporation process at higher pressure and temperature differentials. In the case of handling temperature-sensitive molecules or materials, the pervaporation unit is capable of maintaining any temperature with a lower limit defined by the freezing point of the aqueous media.

For liposome production, the pervaporation unit has been designed to remove non-polar solvents from a predominantly aqueous admixture of water and nonpolar solvent(s), by exposing the fluid admixture to a large surface area of a selectively permeable membrane while the other side of the membrane is exposed to a vacuum, or reduced atmospheric pressure. Selective transmission of nonpolar molecules across the membrane is achieved by the material properties of the membrane itself. In this design, a hydrophobic membrane is used to separate solvent from water because nonpolar solvents will be freely absorbed by the membrane to the exclusion of water, which will remain outside of the membrane material. A laminar flow path or paths that minimize the turbidity of the fluid passing within the device while maintaining a maximal surface contact to a large surface area of the membrane material are used to the greatest extent possible. In this way, solvent droplets are able to reduce in volume to a critical point at which the lipid component of the mixture self-assembles into liposomes, with minimal physical disruption caused by shear force in the form of turbidity. To maximize the transmission of the solvent through the hydrophobic membrane, the pervaporation unit has been engineered to withstand pressure differentials of up to 120 PSI across the exposed membrane surface area as well as the ability to acquire and maintain a preset operating temperature within the range of 20 to 170° F. (−7 to 76° C.).

Like the droplet generator, the pervaporation unit is constructed of materials that are non-corrosive in the presence of water and organic solvents, and cleaning regimens of soap, steam, and/or chlorides. In one embodiment, the unit is designed to be serviced and can be disassembled or otherwise opened to allow the selectively permeable membrane to be accessed and replaced in the event it becomes fouled or otherwise rendered unusable.

Figure 10:
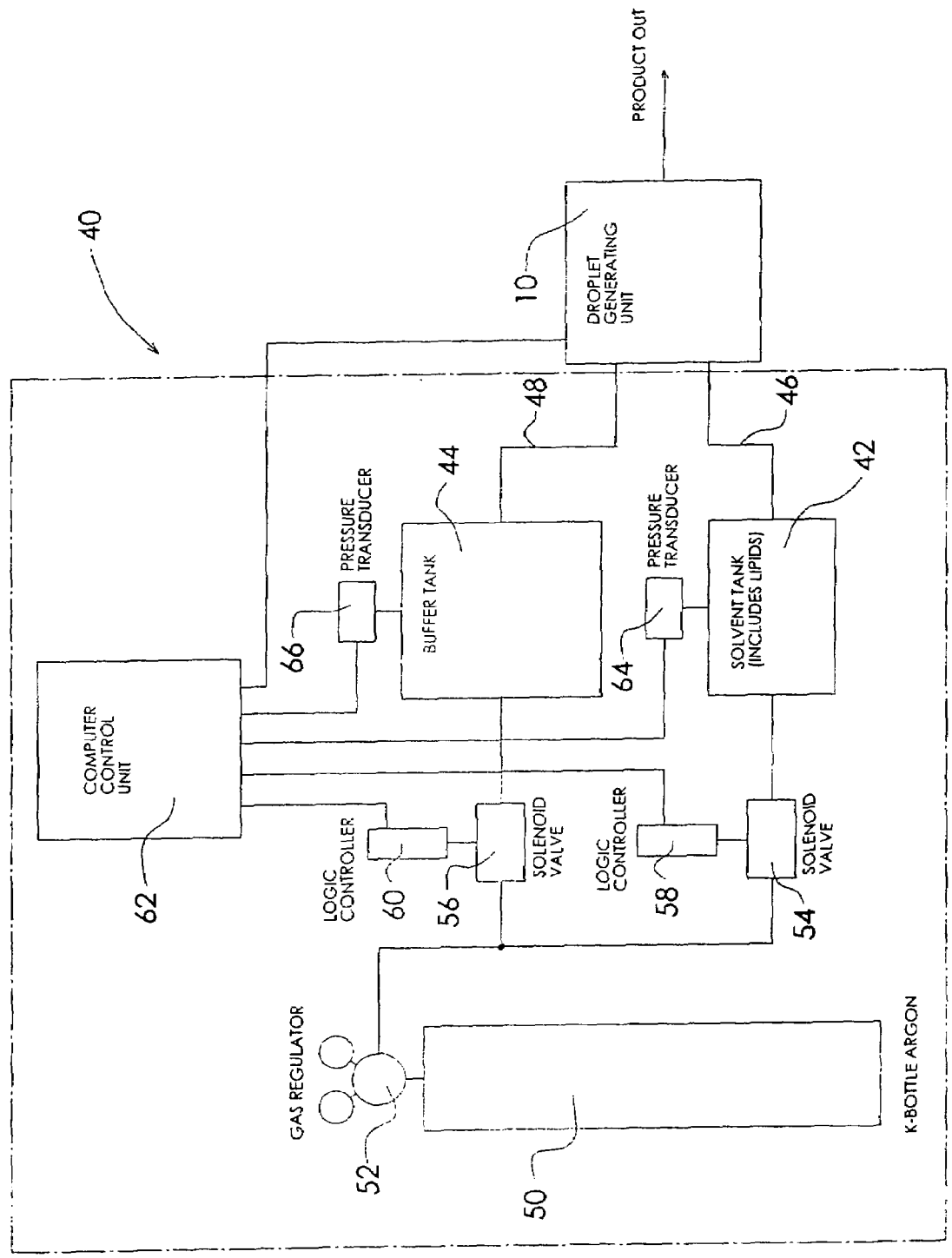
FIG. 10 is a schematic diagram illustrating other components (reservoirs, pumps, logic controls, etc.) of one embodiment of an apparatus according to the present invention.

FIG. 10 illustrates one embodiment of a system for delivering pressurized liquids to a droplet generator. The system 40 includes first and second liquid storage tanks 42, 44, which hold, respectively, the first liquid (e.g., an organic solvent from which droplets are formed) and the second liquid (e.g., water or another aqueous medium). For liposome formation, the lipids that will self assemble are also present in the first liquid storage tank, in low concentration. The contents of these tanks are coupled to the droplet generating apparatus 10 by lines 46 and 48 respectively. A gas tank 50, preferably filled with an inert gas, such as argon, neon, helium, etc., is coupled to a gas regulator 52, which in turn is coupled to a pair of solenoid valves 54 and 56. Preferably, each solenoid valve has a small, muffled orifice. The valves allow pressurized gas to be metered into the liquid storage tanks and thereby drive the feed of liquids into the droplet generating unit.

The solenoid valves are coupled to logic controllers 58 and 60 coupled to a computer control unit (e.g., a microprocessor, CPU, computer, etc.) 62, which is coupled to the droplet generating unit and to a pair of pressure transducers 64, 66 associated with the liquid storage tanks 42, 44. (Alternatively, the logic controllers for the solenoid valves are part of the computer control unit.) System commands (i.e., commands for activating/deactivating the nozzle actuator(s) associated with the droplet generator; for controlling the first liquid pressure/flow through the inlet port in the droplet generator; etc.) can be input into the control unit to operate the overall system. A power supply (not shown) is also provided to drive various electrical components of the system.

By controlling the concentration of lipids in the first liquid, the pressures of the first and second liquids, and the size of the droplets generated in the droplet generator, and by carefully removing the first liquid downstream of the droplet generator, a collection of substantially uniformly sized liposomes, having a mean diameter, D, is formed. Collections of other substantially uniformly sized small particles are prepared in an analogous manner.

Advantageously, the method and apparatus described herein open the door to site-specific biological vectors, i.e., compositions for delivering a therapeutic payload to a patient, in particular, a collection of substantially uniformly sized liposomes sufficient in quantity to be administered as a therapeutic delivery system.

Liposome size is a function of the number of molecules comprising the liposome. Likewise, any small particle is sized according to the chemistry and quantity of material comprising the particle, provided, of course, that the material is compacted or otherwise shaped or oriented in such a way that size is a direct function of material volume. Beginning with a specific concentration of solute in a suitable solvent (e.g. lipids in chloroform), each droplet of a specified size will have the same number of lipid molecules distributed in it. Upon removal of the solvent, each liposome or other particle will have substantially the same number of molecules in it, with a variance that is linearly related to the variance in the volume of the droplets. Thus, if the droplets vary in volume by 2-3%, and they are made of the same solution, then particles derived from these droplets will also vary in solute material content and thus, size, by 2-3%.

Controlling particle/liposome size is therefore a function of controlling droplet size and solute concentration. Droplet size is controlled by using nozzles having substantially uniformly sized and shaped ejection orifices, and by adjusting the electrical pulse creating the droplets. The latter is a fine-tuning technique. In one embodiment, droplet volume is corrected (brought toward normality) by up to 10% by adjusting the electrical pulse(s) that drive the nozzle actuator(s). This is similar to the way inkjet printers are adjusted to ensure that each droplet of ink is the same size. In the embodiment shown in FIG. 2, there are 64 nozzles, and each one has a "fingerprint" of sorts. To ensure that each nozzle produces, e.g., a 10 pL droplet, rather than 9 pL droplet, The voltage or current in the pulse wave to the nozzle's actuator is adjusted as necessary. This can be done iteratively. In one embodiment, the apparatus further includes a feedback mechanism in which a computer and particle size detector are used to measure droplet size, compare it to a desired value, and then adjust the electric pulse(s) driving the actuator(s) to correct droplet size as necessary.

One can calculate the size of a particle containing a specified number of molecules if the density or the area in space occupied by a given molecule is known or can be determined. This information can then be used to calculate a specific droplet size, and the corresponding volume of solvent in each droplet will determine the concentration of the starting solvent solution. In theory, particles nearly as large as the droplets themselves can be formed by using very concentrated solutions, at least in the case where the particles are solid, i.e., not liposomes. At the other extreme, very dilute solutions can yield very small particles, e.g., a 100 nm diameter liposome containing just 300,000 lipid molecules is prepared from a very dilute solution of lipids in solvent. Solute concentration can be adjusted directly, by adding additional solute to solvent or by diluting the solution with additional solvent.

In one embodiment of the invention, a relatively concentrated solution of solute in solvent (e.g., lipids in chloroform) is prepared and stored in a first tank. A second tank contains neat solvent (e.g., chloroform). The two tanks are coupled to the droplet generator by one or more conduits and valves which, in turn, are coupled to the system's logic control, so that precise amounts of the solution and solvent can be metered out as needed. The ratio of the solution and neat solvent can be automatically adjusted to produce any desired concentration of solute in solution, from very rich to very dilute. Each of the nozzles can then be selected to eject a particular sized droplet (plus or minus some variance). Alternatively, a variable solvent system is combined with a series of different sized droplet generators, making it possible to achieve any range of particles from big to small, i.e., 5 nm to 100 micrometers for solid particles, and 20 nm-1 micrometer for liposomes.

Advantageously, the process is digital. A computer or other microprocessor issues an electric pulse and a particle is ultimately ejected from the machine. This is a tremendous improvement over the analog processes of open loop hydrodynamic focusing or the condensation reactions that other particle manufacturers use because, in a given run, one will know exactly how many particles were made. Counting very small particles is a serious technical challenge. Ideally, to count the particles in a sample, one might run the entire sample through a particle detector and, each time a particle was detected, an electric pulse would be sent to a counter. The present invention essentially proceeds in the reverse fashion, and thus provides both a particle maker and counter all in one.

The precise control of particle size by the method and apparatus described herein, and the use of substantially inert materials such as stainless steel, allow the invention to be used to form substantially uniformly sized liposomes as well as a wide variety of other materials. The following nonlimiting examples demonstrate the breadth of possible material combinations, as well as their applicability to a number of industries.

Example 1

Emulsions

One example of a useful material combination is an emulsion of hydrophobic material in an aqueous medium. This is achieved by ejecting droplets of oil, lipid, or other hydrophobic, liquid material into a laminar flow of water or other aqueous media, thereby forming an emulsion or dispersion of fine droplets. The preparation of substantially uniformly sized small droplets should make it possible to achieve emulsions that are far more stable than emulsions produced by other means because the uniformly sized droplets tend to distribute the forces of agglomeration. The hydrophobic particles are suspended in an aqueous fluid as, or as part of, the final product. Such a material is in demand by the medical industry and is useful as a drug preparation. Particles are produced at elevated or lowered temperatures depending on the viscosity of the first and second fluid, with the optimum operating temperature determined empirically. A variation on this example utilizes water or another aqueous medium as the first fluid, while the second fluid is a hydrophobic material with or without a solvent component.

Example 2

Uniformly Sized Phospholipid Liposomes

A droplet generator having 15 micrometer diameter nozzles generates droplets that are 10 pL in diameter and will divide up a liter of chloroform into 1e11 droplets. It will make 1e11 100 nm liposomes. A lipid occupies about 0.4 nm in area in a single layer in a membrane. A 100 nm diameter liposome has an outer (½ bilayer) membrane area of 31,400 sq nm. Thus, there are 78,500 lipids in the outer layer. The bilayer membrane is about 5 nm thick, and the inner spherical layer is thus 90 nm in diameter. The inner layer has 25,400 sq nm and thus 63,500 lipid molecules in it. There are therefore 142,000 lipids in this 100 nm liposome.

To make 1e11 100 nm liposomes, 1e11×142,000 lipid molecules are added to one liter of chloroform, with stirring. The molecular weight of a certain phosphatidylethanolamine ($C_{41}H_{83}NO_8P$) is 749.07), therefore [(1e11)(142,000)(749.07)/(6.022e23)]=0.0000177 grams of lipids are used to make a liter of 2.3e-8 M solution. The solution comprises the "first liquid" in the droplet generator. The second liquid is aqueous, with a small quantity of buffer. The resulting droplets that are formed are passed through a pervaporation unit until substantially all of the chloroform is removed, yielding a collection of substantially uniformly sized (100 nm) liposomes in water.

Example 3

Nanodots

Very small, uniformly sized crystals are made from suspensions of dissimilar fluids. For example, crystals of inorganic materials such as gallium arsenide, zinc sulfide, and indium phosphate are made by dissolving ionic material or their precursors into a first, heated, aqueous fluid, then ejecting droplets of the impregnated fluid into a second, hydrophobic fluid, such as an oil. By reducing the water content to a desired fraction at a given rate, and reducing the temperature of the combined fluid emulsion, it is contemplated that crystals having a tightly constrained size will form. In particular, the size of the crystals will be dependent on the concentration of starting ions or other solutes in the first, aqueous fluid, the volume of the fluid droplets of the first fluid, the fraction by which the droplets of the first fluid are reduced, and the operating temperature. Particles are produced at elevated or lowered temperatures depending on the viscosity of the first and second fluid, with the optimum operating temperature determined empirically. These particles are suspended in a hydrophobic fluid, such as an oil, which can be removed by filtration and washing steps. This material is in demand by the biotechnology and medical diagnostics industries for use as, e.g., labels (markers).

Example 4

Solid Polymer Beads

Beads of polystyrene and other polymers are produced by mixing one or more polymers with a first fluid (a hydrophobic solvent), and ejecting the impregnated fluid into water or another aqueous second fluid. The size of the particles is controlled by the proportion of polymer(s) in the first fluid and the size of the droplets that are generated. Upon removal of a sufficient quantity of the solvent component of the first fluid, solid polymer beads are generated. The particles are sized by adding more or less solvent in the first fluid, by varying temperature, and also by controlling initial droplet size.

The volume of a 100 nm sphere is 523,598 $nm^3$. There are 1e-8 nm in a cm, and there are therefore 1e24 cubic nm in one cubic cm. For polystyrene having a density of 10.5 grams per cubic cm, there are [(10.5 g)(523,598)/(1e24 nm3)]=5.5e-18 grams of styrene per particle. Thus, (5.5e-18)(1e11)=5.5e-7 grams of styrene are added to one liter of solvent, with stirring, to make 1e11 polystyrene spherical particles having a diameter of 100 nm.

Particles are produced at elevated or lowered temperatures depending on the viscosity of the first and second fluid, with the optimum operating temperature determined empirically. These particles are suspended in water, which can be removed by filtration and evaporation. This material is in demand by the biotechnology and medical diagnostics industries as, e.g., a laboratory tool.

Example 5

Magnetic Beads

Small, uniformly sized magnetic beads are produced by mixing ferrite with a polymer matrix material, e.g., polystyrene, in a solvent (thereby forming the first fluid), and ejecting droplets of the first fluid into a second fluid. Magnetic beads are produced upon removal of the solvent component of the first fluid. The particles are sized by adding more or less solvent in the first fluid, by varying temperature, and also by controlling initial droplet size. Particles are produced at elevated or lowered temperatures depending on the viscosity of the first and second fluid, with the optimum operating temperature determined empirically. These particles are suspended in water, which can be removed by filtration and evaporation. This material is in demand by the biotechnology and medical diagnostics industries.

Example 6

Oil-Filled Beads

Particles containing a hydrophobic fluid are produced by mixing an oil or other hydrophobic, non-volatile fluid, a polymer, and solvent as the first fluid, and then ejecting the fluid as droplets into a second fluid composed of water and a crosslinking agent, thereby forming a fluid-filled bead having a solid external shell. The method is useful for entrapping an oil or oil-like fluid into small spherical rigid vesicles. The particles are sized by adding more or less solvent in the first fluid, and also by controlling initial droplet size. Particles are produced at elevated or lowered temperatures depending on the viscosity of the first and second fluid, with the optimum operating temperature determined empirically. The particles are suspended in water, which can be removed by filtration and evaporation. This material is in demand by the electronics industry for such applications as polymer-dispersed liquid crystals (PDLC).

The invention has been described with reference to various embodiments, figures, and examples, but is not limited thereto. For example, in another aspect of the invention, particles having externally modified surfaces are prepared by incorporating external elements, known as fluors, in the second fluid. The fluors chemically interact with, and become bound to, the small particles as they form. For example, the surfaces of uniformly sized small beads can be modified by any number of chemical processes, including etching, coating, and ligand attachment, by mixing the compounds for those processes into the second fluid. The beads can be further modified in one or more subsequent steps by adding fluids in-line, downstream of the described particle forming processes, and by adding any number of additional linear or batch processing steps. Persons having ordinary skill in the art will appreciate that the invention can be modified in a still other ways without departing from the invention, which is limited only by the appended claims and equivalents thereof.

What is claimed is:

1. An apparatus for making substantially uniformly sized particles, comprising:
   a first liquid inlet channel;
   a second liquid inlet channel;
   a liquid outlet channel;
   a plurality of transverse liquid channels extending from the first liquid inlet to the liquid outlet channel;
   a plurality of nozzles in liquid flow communication with the plurality of transverse liquid channels and the second liquid inlet;
   one or more nozzle actuators coupled to the plurality of nozzles; and
   an evaporator coupled to the liquid outlet channel, wherein each nozzle has an ejection orifice diameter of from about 0.03 μm to 50 μm, and wherein the plurality of nozzles includes ejection orifice diameters capable of producing uniformly sized particles that vary in diameter by no more than 3%.

2. An apparatus as recited in claim 1, wherein each of the plurality of nozzles is coupled to a corresponding one of the plurality of transverse liquid channels.

3. An apparatus as recited in claim 1, wherein each of the plurality of nozzles extends into a corresponding one of the plurality of transverse liquid channels.

4. An apparatus as recited in claim 1, wherein each of the plurality of transverse liquid channels has a channel bed, each of the plurality of nozzles has a distal end, and the distal end of each nozzle is substantially flush with the channel bed of a corresponding one of the plurality of transverse liquid channels.

5. An apparatus as recited in claim 1, wherein the evaporator comprises a membrane pervaporation unit.

6. An apparatus as recited in claim 5, wherein the membrane pervaporation unit includes a solvent-permeable ceramic membrane.

7. An apparatus as recited in claim 5, wherein the pervaporation unit is coupled to the liquid outlet channel via a collection reservoir or conduit.

8. An apparatus as recited in claim 1, wherein the evaporator comprises an open reservoir.

9. An apparatus as recited in claim 1, wherein the nozzle actuators comprise piezoelectric actuators.

10. An apparatus as recited in claim 1, wherein the nozzle actuators comprise thermal bubble actuators.

11. An apparatus as recited in claim 1, further comprising a thermoelectric cooler.

12. An apparatus as recited in claim 1, further comprising a thermal radiator.

13. An apparatus as recited in claim 1, further comprising a first liquid reservoir, coupled to some or all of the nozzles.

14. An apparatus as recited in claim 1, wherein the first liquid reservoir is coupled to all of the nozzles.

15. An apparatus as recited in claim 1, further comprising a liquid reservoir coupled to the liquid inlet channel.

16. An apparatus as recited in claim 1, further comprising a first liquid reservoir coupled to all of the nozzles, and a second liquid reservoir coupled to the liquid inlet channel.

17. An apparatus as recited in claim 16, further comprising a pressurization system for moving liquids from the first and second reservoirs into the nozzles and liquid inlet channel, respectively.

18. An apparatus as recited in claim 1, wherein each nozzle has an ejection orifice diameter of from 5 μm to 25 μm.

19. An apparatus for making substantially uniformly sized particles, comprising:
   a first liquid inlet channel;
   a second liquid inlet channel;
   a liquid outlet channel;
   a plurality of transverse liquid channels extending from the first liquid inlet to the liquid outlet channel;
   a plurality of nozzles in liquid flow communication with the second liquid inlet channel and the plurality of transverse liquid channels;
   one or more nozzle actuators coupled to the plurality of nozzles; and
   an evaporator coupled to the liquid outlet channel,
   wherein each nozzle has an ejection orifice diameter of from about 0.03 μm to 50 μm, and the plurality of transverse channels are capable of sustaining laminar fluid flow and wherein the plurality of nozzles includes ejection orifice diameters capable of producing uniformly sized particles that vary in diameter by no more than 3%.

* * * * *